United States Patent
Agee

(10) Patent No.: US 6,208,892 B1
(45) Date of Patent: *Mar. 27, 2001

(54) TIME DOMAIN ULTRA-WIDE BAND RF-ENHANCED CHEMOTHERAPY FOR CANCER TREATMENT

(75) Inventor: Forrest J. Agee, Albuquerque, NM (US)

(73) Assignee: The United States of America as represented by the Secretary of the Air Force, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/277,593

(22) Filed: Mar. 26, 1999

(51) Int. Cl.[7] ....................................................... A61N 1/30
(52) U.S. Cl. .................................. 604/20; 607/74; 600/14
(58) Field of Search ............................. 604/20; 600/411, 600/14; 607/1, 88, 72–74

(56) References Cited

U.S. PATENT DOCUMENTS

| 5,386,837 | * | 2/1995 | Sterzer | 128/898 |
| 5,690,109 | * | 11/1997 | Bovind et al. | 607/411 |
| 5,908,444 | * | 6/1999 | Azure | 607/88 |

* cited by examiner

*Primary Examiner*—Anhtuan T. Nguyen
(74) *Attorney, Agent, or Firm*—Kenneth E. Callahan

(57) ABSTRACT

The ultra-wide band rf-enhanced chemotherapy for treatment of cancer and other intracellular diseases provides for increasing drug effectiveness. It also provides a means of treatment of inoperable cancers. The invention uses ultra-wide band short pulses to provide high electric field strength in diseased areas of a patient to induce electroporosis preferentially in the region to be treated by chemotherapy. The effect is to make the interiors of the cells in the affected region open to the chemotherapeutic agent. The treatment can be enhanced in its effectiveness thereby. It also enables treatment with reduced doses of the therapeutic agent and reduces side effects in other areas of the patient through the reduction of the total dosage. The invention makes specific use of the polarization of UWB fields and the very short duration of the pulsed electromagnetic fields induced into the region to be treated to minimize the absorbed rf energy associated with the treatment, making the heating of tissue negligible. The invention also makes it possible to select the size of the region being treated and in some embodiments to move the treated region electronically.

8 Claims, 2 Drawing Sheets

TIME DOMAIN ULTRA-WIDE BAND RF-ENHANCED CHEMOTHERAPY FOR CANCER TREATMENT

BACKGROUND OF THE INVENTION

1. Field of the Invention

This invention is in the field of electroporosis, and relates in particular to time domain methods for generating electromagnetic fields in the interior of the body to improve delivery of therapeutic drugs to the body's cells.

2. Description of the Prior Art

Electroporosis is the process wherein cell membrane pores are opened through the application of electromagnetic fields. For example, Dr. Diane Gaylor of MIT has demonstrated electroporosis of normal skeletal muscle cells at electric field gradients as low as 2.5 kV per meter. Inoperable cancers are frequently treated by chemotherapy, ionizing radiation, or combined radiation/chemotherapeutic modalities. A central limitation of chemotherapeutic effectiveness is the inability of the chemical agent to penetrate into the tumor tissue, and especially into the tumor cell, thus resulting in resistance to therapy. Dr. Mir in France has experimentally determined that electroporation of cancer cells can increase the influx of chemotherapeutic agents into those cells by more that 50 fold. He has also demonstrated that this effect appears useful in treatment of human patients with inoperable cancer in cases where electrodes can be placed on the skin on opposite sides of the tumor. In these treatments the patient is pre-loaded with an orally administered chemotherapeutic agent and the locally imposed electromagnetic field is believed to increase tumor uptake of the agent through the process of membrane electroporation.

Other diseases suffer the same difficulty of getting the therapeutic drug to the target site. For example, diseases based on the existence of intracellular organisms, such as viruses or parasites, are frequently resistant to drug therapy because of failure of the medicine to penetrate the cells. Other examples include the inability of AZT to penetrate the immune cell in the treatment of AIDS, the difficulty in treating another viral ailment, cytomegalic inclusion disease, and Chagas disease, a parasitic infestation.

While electrodes have been used to generate sufficient electromagnetic fields for electroporosis near the surface, they can not effectively reach tumors deep within the human body. Electrodes can easily be used when the tumor is superficial. However, electrodes require surgical procedures if they are to be used within the body.

U.S. Pat. No. 5,386,837 teaches a method of applying pulses of high-frequency force fields (rf, microwave, high-energy infrared, laser electromagnetic wave energy, or ultrasonic acoustic energy) to portions of the human body for the purpose of making those portions more susceptible to chemotherapeutic drugs. One or more applicators deliver energy such that at the site at which these beams intersect, the intensity is sufficient to open the cell.

The '837 patent differs from this invention in several ways. The cited patent uses heat inducing sources. The present invention uses ultra-wide band (UWB) sources that are polarized time domain pulses that locally raise the field strength in the region of a tumor to a level sufficient to induce electroporosis. The use of UWB pulses also inherently provides for very low rf energy being used to induce electroporosis, the energy being limited to that associated with short pulses on the order of picoseconds to nanoseconds. This avoids tissue heating. The use of UWB pulses at a very low pulse repetition frequency also avoids osmotic shock, the rupture of cells when exposed to high field strength or too much exposure. Holding the cell walls open can result in an inability to close the pore and results in cell rupture.

SUMMARY OF THE INVENTION

The present invention overcomes the deficiencies of the prior art by providing both method and apparatus for treating tumors deep within the human body. Electroporosis is induced within a portion of the body through the use of an ultra-wide band pulser-driven transmission line, antenna, or antenna array. Chemotherapy can be applied either orally, by venous injection, or by local injection into the tumor via arterial catheter, in some cases enclosed within microscopic casings that open in high fields.

It is, therefore, an object of the present invention to provide an enhanced treatment for inoperable cancers by providing devices and associated techniques for the improved delivery of chemotherapeutic drugs to the diseased cells.

It is another object of the present invention to improve the delivery of chemotherapeutic drugs to cells in the case of diseases other than cancer, such as viral or parasitic infections.

It is a further object of the present invention to improve the ability to perform medical cellular research by increasing the ability to deliver chemicals directly into the cell interior.

It is a further object of the invention to provide a precise way of selectively enhancing chemotherapy in limited portions of a patient that are diseased.

DESCRIPTION OF THE PREFERRED EMBODIMENT

Chemotherapy, ionizing radiation, or the combination of radiation and chemotherapeutic modalities are frequently used to treat inoperable cancers. The chemotherapeutic effectiveness is limited by the inability of the chemical agent to penetrate into the tumor tissue and especially into the tumor cell. The present invention proposes to engender electroporosis in tumors deep within the human body that are not reachable by electrode techniques.

Figure 1:
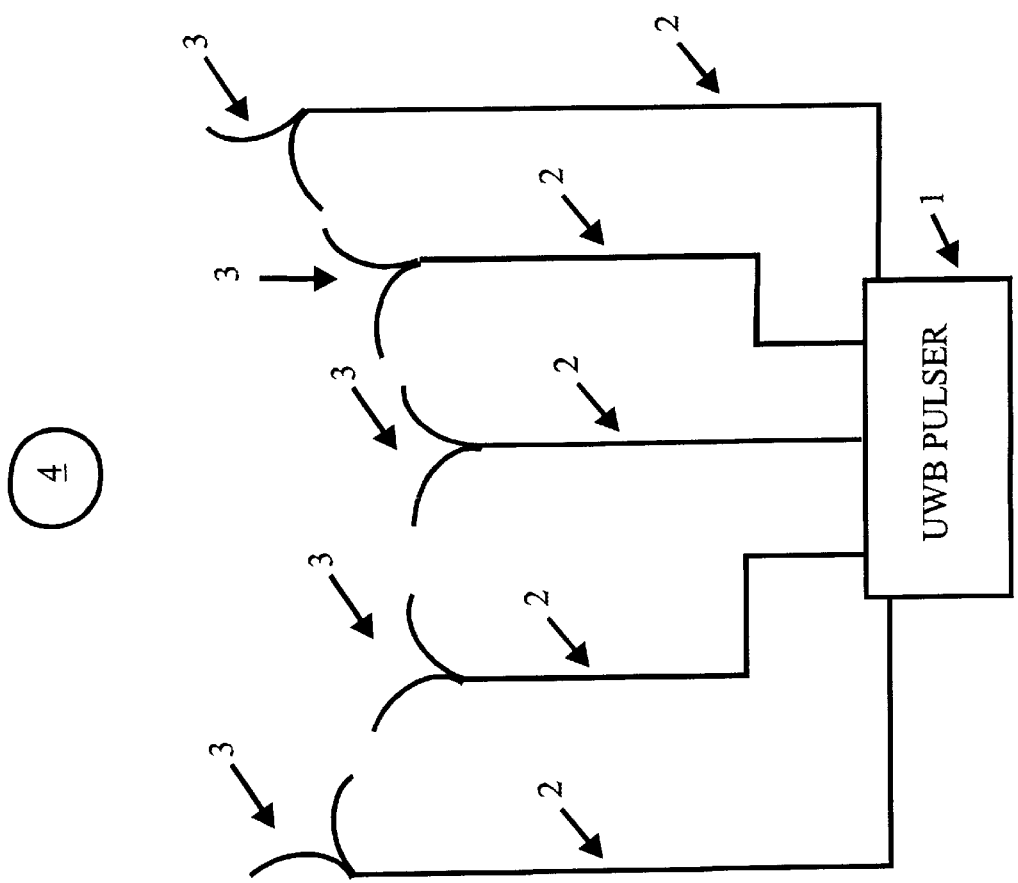
FIG. 1 shows a UWB pulser that is attached to multiple antennas by cables that along with the antenna locations provide a means of synchronizing the arrival time of the pulsed electromagnetic fields to produce a localized field.

The first embodiment of the present invention is shown in FIG. 1. This consists of an array of antennas driven by an ultra-wideband (UWB) high-power microwave pulser 1 featuring very fast rise time pulses. The pulser is connected by cables 2 to the antennas 3. The length of the cables and the distance from the antennas to the tumor are used to affect simultaneous arrival of the pulses at the tumor or area to be treated. The rise time of the UWB pulser is on the order of 10 to 100 picoseconds (ps). The peak field strengths in the high field region 3 obtained are in the range of 10–100 kilovolts per meter (kV/m) and pulse lengths are on the order of 10 ps to a few nanoseconds (ns) depending on the area of the patient to be treated. The patient is introduced into the region of the apparatus that is synchronized for simultaneous arrival of the pulsed electric fields so that the tumor is in the high field region. The speed of light is 1 ft/ns, which provides the ability to use timing of the pulses, duration of the pulses, and polarization of the pulses to create a high field region that can be spatially controlled to coincide with the portion of the patient to be treated. When the pulse length is increased, the area of the high field increases due to the space-time relationship provided by the speed of light, 1 ft/ns. For example, 250 ps pulses can be arranged to provide a high field region of the dimension approximately 3 inches.

Figure 2:
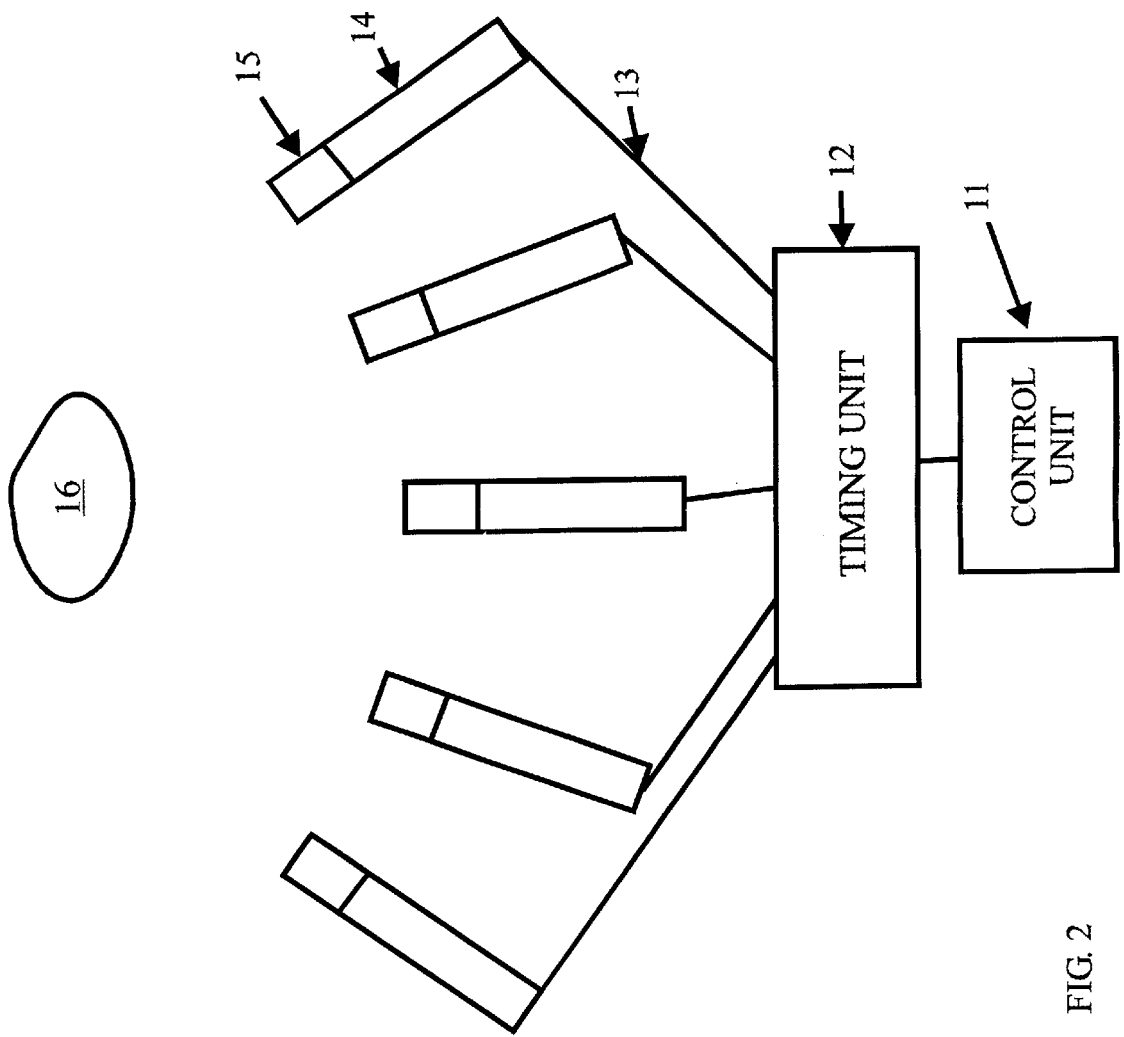
FIG. 2 is an array of ultra-wide band emitters whose timing is controlled to provide a localized high electromagnetic field.

When narrow beam (1° beam width) impulse radiating antennas (IRAs) are used, the beam intersections as well as the timing and antenna location contribute to the localization of the high field region. For this case, FIG. 2 shows the IRAs 13 attached to the pulser 11 through cables 12. FIG. 2 shows the IRAs 15 driven by pulsers 14.

Chemotherapy is administered in one of three ways. The chemical or drug can be administered orally in a manner such that a maximum chemical exposure baths the tumor at the time of the electromagnetic exposure, typically about 20 minutes after ingestion. A second option that in most cases is preferred over oral administration has the drug placed into the patient by injection into the brachial or femoral vein. In this case, circulation time to the tumor surface will be approximately a few minutes and high local transient concentrations will be achieved. The most desirable approach would employ catheterization of a tumor vessel and direct local exposure of the tumor to a chemical agent while the tumor is receiving the pulsed electromagnetic field.

Thus, the application of the electromagnetic field could be about 20 minutes after the oral administration of a chemical agent, one to five minutes after the intravenous injection of a chemical, or simultaneous with the catheter delivery of the chemical. The electromagnetic treatment is envisaged to last 20 minutes with repeated pulsing to take advantage of chemical diffusion times and the time during which a cell membrane pore will remain open after formation by an electromagnetic field. The pulse repetition frequency (PRF) need be no more than needed to open the cell pores occasionally to admit the chemotherapeutic agent. The low pulse repetition frequency allows the cells to open pores and close them, while the combination of a low PRF and short pulses minimizes the patient's exposure to rf energy. A typical pulse repetition frequency would be a pulse every two minutes or a range of 0.1 to 0.001 Hz.

A novel but as yet unproved delivery means is that developed by Dr. Robert Liburdy of Lawrence Livermore Laboratories. He produced microscopic lipid saccules that carry chemotherapeutic agents and rupture in high peak electromagnetic fields, thus delivering high local concentrations of agents. This technique would benefit both from the action of the pulsed electromagnetic field for the purpose of releasing the agent in the vicinity of the tumor and also by enhancing penetration of the agent and its tumor killing effectiveness.

In FIG. 2 a control unit 11 is used to control a timing unit 12 that uses electrical cables or fiber optic cables 13 to activate an array of ultra-wide band pulsers 14 that drive an array of antennas 15. The array is arranged to provide ultra-wide band pulses of polarized rf energy sufficient to generate 10–100 kV/m fields in region 16. The patient is located so that the tumor is more or less centered within the high field region 16. The region being treated can be changed readily by changing the array timing. The polarization of the antennas is arranged to cause the electromagnetic fields to add in the region to be treated (e.g., vertical polarization). The short pulses allow the region to be treated to be small and the pulse width, timing of the array, and location of the antennas allow the region to be treated to be precisely controlled. This can be further enhanced by the use of narrow beam impulse radiating antennas.

The techniques described herein generate sufficient electromagnetic fields to permit electroporosis of deep-seated internal tumors. Electroporosis can thereby be induced in the tumor preferentially over other parts of the body. A further benefit is that the need for contact with the skin by electrodes is eliminated. This is important when treating painful cancers, such as cancer of the pancreas, where even wearing normal clothing can be painful.

The use of linearly polarized, short pulses makes the thermal heating associated with other microwave sources negligible, and it avoids wholesale damage of cells by enabling the cells to open pores and then close them. The disclosed techniques increase the amount of chemical agent absorbed in the desired region while reducing the total dose of agent required to treat the patient. Higher local doses to the cancer substantively increase the probability of cure. The lower total doses to the body as a whole reduce chemical side effects.

This invention will potentially increase the range and type of cancers that can be treated by chemotherapy. It will allow treatment of certain cancers that cannot now be effectively treated by surgery, radiation, chemotherapy, or combinations of these modalities, e.g., glioblastoma multi form. Additional specific cancer targets include, but are not restricted to, cancer in the tail of the pancreas, hepatocarcinoma, and nonresectable colonic adenocarcinoma.

It will be apparent that many modifications and variations may be implemented without departing from the scope of the novel concept of this invention. Therefore, it is intended by the appended claims to cover all such modifications and variations which fall within the true spirit and scope of the invention.

We claim:

1. In an electroporosis treatment, an apparatus providing the required high electromagnetic field region at a desired location in a patient's body, said apparatus comprised of:

a) an array of like-polarized antennas;

b) an ultra-wideband (UWB) high-power microwave pulser outputting polarized pulses with rise times of 10 to 100 ps, pulse lengths of 10 ps to several nanoseconds, and of sufficient power to provide peak field strengths in the high field region of 10 to 100 kV/m; and c) a cable connecting said UWB pulser to each antenna in said array of antennas such that the length of each cable and the distance of each antenna from the desired location of the high field region causes the pulses to simultaneously arrive and add together in the desired location.

2. The apparatus of claim 1, wherein the pulse lengths are varied to create a high field region that encompasses the desired volume.

3. The apparatus of claim 1, wherein the array of like-polarized antennas consists of impulse radiating antennas with beam widths of about one degree.

4. The apparatus of claim 1, wherein said pulses have a pulse repetition frequency of 0.1 Hz to 0.001 Hz, thereby allowing the cell pores to open to accept chemotherapeutic agents and then close between pulses.

5. In an electroporosis treatment, an apparatus providing the required high electromagnetic field region at a desired location in a patient's body, said apparatus comprised of:

a) an array of like-polarized antennas;
b) a separate photoconductively-switched ultra-wideband (UWB) high-power microwave pulser driving each antenna of said array of antennas, each pulser outputting polarized pulses with rise times of 10 to 100 ps, pulse lengths of 10 ps to several nanoseconds, and of sufficient power to provide combined peak field strengths in the high field region of 10 to 100 kV/m;
c) cables connecting each UWB pulser to a timing unit capable of transmitting light pulses to activate said UWB pulsers; and
d) a control unit means to drive the timing unit, such that the pulses transmitted by each antenna simultaneously arrive and add together at the desired location for high field region.

6. The apparatus of claim 5, wherein the pulse lengths are varied to create a high field region that encompasses the desired volume.

7. The apparatus of claim 5, wherein the array of like-polarized antennas consists of impulse radiating antennas with beam widths of about one degree.

8. The apparatus of claim 5, wherein said pulses have a pulse repetition frequency of 0.1 Hz to 0.001 Hz, thereby allowing the cell pores to open to accept chemotherapeutic agents and then close between pulses.

\* \* \* \* \*